(12) United States Patent
Guerret

(10) Patent No.: US 11,945,831 B2
(45) Date of Patent: Apr. 2, 2024

(54) ADDUCTS OF TRIPHENYLPHOSPHINE AND TRIPHENYLPHOSPHITE AND THEIR USE FOR THE BROMINATION OF PRIMARY ALCOHOLS

(71) Applicant: MELCHIOR MATERIAL AND LIFE SCIENCE FRANCE, Lacq (FR)

(72) Inventor: Olivier Guerret, Pern (FR)

(73) Assignee: MELCHIOR MATERIAL AND LIFE SCIENCE FRANCE, Lacq (FR)

( * ) Notice: Subject to any disclaimer, the term of this patent is extended or adjusted under 35 U.S.C. 154(b) by 597 days.

(21) Appl. No.: 17/286,161

(22) PCT Filed: Oct. 21, 2019

(86) PCT No.: PCT/EP2019/078597
§ 371 (c)(1),
(2) Date: Apr. 16, 2021

(87) PCT Pub. No.: WO2020/079281
PCT Pub. Date: Apr. 23, 2020

(65) Prior Publication Data
US 2021/0371438 A1 Dec. 2, 2021

(30) Foreign Application Priority Data
Oct. 19, 2018 (FR) ...................................... 1859688

(51) Int. Cl.
*C07F 9/50* (2006.01)
*C07F 9/06* (2006.01)
*C07F 9/54* (2006.01)

(52) U.S. Cl.
CPC ............ *C07F 9/5022* (2013.01); *C07F 9/062* (2013.01); *C07F 9/54* (2013.01)

(58) Field of Classification Search
CPC .......... C07F 9/5022; C07F 9/062; C07F 9/54; C07F 9/6596; C07C 2601/02; C07C 2601/04; C07C 17/16
See application file for complete search history.

(56) References Cited

U.S. PATENT DOCUMENTS

| | | |
|---|---|---|
| 6,008,420 A | 12/1999 | Komoschinski et al. |
| 6,063,971 A * | 5/2000 | Komoschinski ........ C07C 17/16 570/186 |
| 6,191,300 B1 | 2/2001 | Hyatt |
| 2016/0355452 A1 | 12/2016 | Guerret |

FOREIGN PATENT DOCUMENTS

| | | | |
|---|---|---|---|
| EP | 1 818 336 A1 | 8/2007 | |
| FR | 3 010 997 A1 | 3/2015 | |
| FR | 3010997 A1 | 3/2015 | |
| FR | 3016166 A1 * | 7/2015 | ............. C07C 17/16 |
| JP | 2000-504733 A | 4/2000 | |
| JP | 2002-542228 A | 12/2002 | |

OTHER PUBLICATIONS

International Search Report for International Application No. PCT/EP2019/078597, dated Jan. 16, 2020.
Faul et al., "Cyclization Strategies for the Synthesis of Macrocyclic Bisindolylmaleimides," Journal of Organic Chemistry, vol. 66, No. 6, 2001, pp. 2024-2033.
Hrubiec et al., "Regioselective route to sterically hindered cyclopropylcarbinyl halides," The Journal of Organic Chemistry, vol. 49, No. 3, 1984, pp. 431-435.

* cited by examiner

Primary Examiner — Deborah D Carr
(74) Attorney, Agent, or Firm — Birch, Stewart, Kolasch & Birch, LLP

(57) ABSTRACT

The present invention relates to the use of novel adducts of general formula (I) $TPP_x TPOP_{(1-x)}$, wherein TPP is triphenylphosphine, TPOP is triphenylphosphite and x is a real number between 0.05 and 0.9. These novel adducts are useful for the bromination of primary alcohols, in particular for the bromination of primary alcohols.

14 Claims, No Drawings

ADDUCTS OF TRIPHENYLPHOSPHINE AND TRIPHENYLPHOSPHITE AND THEIR USE FOR THE BROMINATION OF PRIMARY ALCOHOLS

The present invention relates to the use of novel adducts of general formula (I) $TPP_xTPOP_{(1-x)}$, wherein TPP is triphenylphosphine, TPOP is triphenyl phosphite and x is a real number between 0.05 and 0.9. These novel adducts are useful for the bromination of primary alcohols, in particular for the bromination of primary alcohols containing a strained ring with 3 or 4 carbon atoms such as cyclopropylmethanol or cyclobutylmethanol.

More particularly, these adducts are advantageously used in a method for obtaining brominated compounds of high purity under synthesis conditions that enable high productivity for industrial facilities, in particular of bromomethyl cyclopropane (2a) and bromomethyl cyclobutane (2b) of high purity, respectively from cyclopropylmethanol 1a and cyclobutylmethanol 1b. These brominated compounds, in particular compounds 2a and 2b, are synthesis intermediates essential to many active ingredients.

Diagram 1 Structures of compounds 1a,b and 2a,b

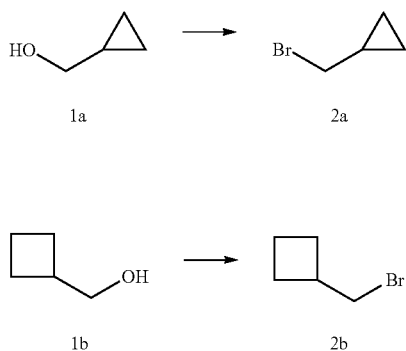

CONTEXT OF THE INVENTION

Due to the high reactivity of cyclopropyl and cyclobutyl strained rings, it is often preferable for the skilled person to use these intermediates in the final steps for preparing active ingredients. As a result, the purity of bromomethyl cyclopropane (BMCP) molecules and bromomethyl cyclobutane (BMCB) molecules is essential since it directly influences the impurity profile of active ingredients. The most difficult to control impurities for BMCP are 4-bromobut-1-ene and bromocyclobutane and for BMCB are 5-bromopent-1-ene and bromocyclopentane, as they have boiling points very close to the target molecules. It is therefore essential that these impurities be controlled before distillation by means of the synthesis conditions.

Recently, two patents have disclosed a production method for BMCP. In patent FR3010997, a method involving, in this order, triphenyl phosphite diluted in dimethyl formamide, dibromide and then carbinol is described. The inventors refer to the passage through a complex allowing the production of a BMCP having a low level of impurities and good productivity.

Triphenyl phosphite, also denoted TPOP, corresponds to the following formula (II):

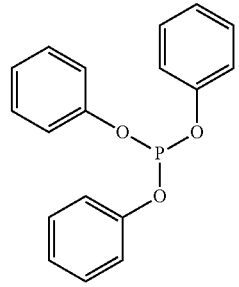

(II)

In patent FR3016166, the applicant describes a method involving the same reactants as previously used under different conditions (temperature, dilution) but also leading to BMCP with a very low level of impurities. The reaction intermediate in the case of this method is a phosphonium salt known to lead selectively to brominations of primary or secondary alcohols (see O. Castro, Organic Reactions, vol. 29 William G Sauben & al., 1983, Organic Reactions, Inc published by John Wiley & Sons Inc. pages 4-25).

Among publications prior to these patent applications, patent U.S. 61/913,001 describes an essentially similar method, with the difference that triphenyl phosphite is replaced by triphenylphosphine and that all the reactants are introduced at the same time into the reactor. This method, with a significant excess of dibromine, leads to ultra pure BMCP.

Triphenylphosphine, also denoted TPP, corresponds to the following formula (III)

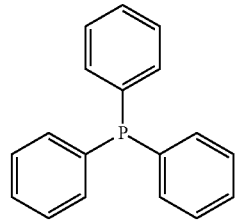

(III)

Yet, due to the evolution of needs in the pharmaceutical industry, specifications have become increasingly stringent. Thus from 0.5% by weight, relative to the total weight, of 4-Bromobut-1-ene tolerated in BMCP, the manufacturers of active ingredients have set new limits at 0.2% by weight, relative to the total weight.

Patent U.S. 61/913,001 describes a method for achieving these specification levels, which reflects a greater selectivity of the adduct formed between triphenylphosphine and dibromine than that of the adduct formed between the triphenyl phosphite and dibromine. However, the method of this patent U.S. 61/913,001 is not productive due to the poor solubility of triphenylphosphine in DMF. Such a problem is illustrated in the third example of patent FR3016166.

Moreover, in a sector increasingly subject to international competition, increasing reaction productivity is an essential advantage to retain market share.

Surprisingly, the applicant found that the use of an adduct of general formula $TPP_xTPOP_{(1-x)}$ wherein x is a real number comprised between 0.05 and 0.9 in a bromination process with dibromine leads to higher yields and improved productivity relative to the use of either TPP alone or TPOP alone.

Since the reactivity of strained rings is particularly tricky, it will be easily understood that the use of these adducts in a bromination process can be applied to bromination of all primary alcohols.

BRIEF DESCRIPTION OF THE INVENTION

According to a first embodiment, the invention concerns an adduct of general formula (I)

$$TPP_xTPOP_{(1-x)} \tag{I}$$

wherein
TPP designates triphenylphosphine;
TPOP designates triphenyl phosphite; and
x is a real number comprised between 0.05 and 0.9.

The invention also relates to an adduct according to the first embodiment, for which x is comprised between 0.05 and 0.5, especially 0.1 and 0.5.

The invention also relates, according to a third embodiment, to a preparation method for the adduct according to embodiment 1 or 2, wherein x parts by mole of triphenylphosphine and (1-x) parts by mole of triphenyl phosphite are mixed at a temperature Tx comprised between 20° C. and 50° C.

The invention also relates, according to a fourth embodiment, to a preparation method according to embodiment 3 in which Tx equals 25° C. and x<0.5.

In a fifth embodiment, the invention relates to the use of an adduct according to embodiment 1 or 2 or the adduct obtained by the method according to embodiment 3 or 4 as a liquid bromination agent for primary alcohol.

The invention also relates, in a sixth embodiment, to a use according to the previous embodiment, in which the primary alcohol comprises a hydrocarbon ring with 3 or 4 carbon atoms, in particular the primary alcohol is cyclopropylmethanol or cyclobutylmethanol.

According to a seventh embodiment, the invention concerns a preparation method for a brominated compound by bromination of primary alcohol comprising the following steps:
1. mixing (a) 1 molar equivalent of adduct (I) according to the invention or the adduct obtained by the method according to the invention and (b) 1 to 3 volumes of polar solvent; then
2. Adding the dibromine:
   2.1 cool with stirring the solution obtained in step 1) to a temperature comprised between 0° C. and 12° C., then
   2.2 to the cooled solution obtained after step 2.1), add between 1.05 and 1.25 molar equivalents of dibromine while keeping the reaction medium temperature below 12° C.; then
3. Adding the primary alcohol:
   3.1 following step 2.2), lower the reaction medium temperature to a value comprised between 0° C. and -15° C.;
   3.2 to the cooled reaction medium obtained following step 3.1), add between 0.95 and 1 molar equivalent of primary alcohol, then
4. Recovering brominated compound (A).

Another subject of the invention, in an eight embodiment, is to provide a method according to embodiment 7, wherein the polar solvent is chosen from among dimethylformamide, dimethyl sulfoxide, sulfolane, dichloromethane, tetrahydrofuran, dimethyl glycol ether, dichloroethane, acetonitrile, and mixtures thereof.

According to a ninth embodiment, the invention also concerns a method according to embodiment 7 or 8, wherein during step 2.2) the reaction medium is maintained at a temperature comprised between 0° C. and 12° C.

In a tenth embodiment, the invention also relates to a method according to any of embodiments 7 to 9, wherein during step 3.2) the reaction medium is maintained at a temperature comprised between 0° C. and -15° C., and advantageously comprised between 0° C. and -5° C.

According to an eleventh embodiment, the invention concerns a method according to any of embodiments 7 to 10 wherein the primary alcohol comprises a hydrocarbon ring with 3 or 4 carbon atoms.

According to a twelfth embodiment, the invention also relates to a method according to any of embodiments 7 to 11 wherein the primary alcohol is cyclopropyl carbinol.

According to a thirteenth embodiment, the invention further relates to a method according to any of embodiments 7 to 11 wherein the primary alcohol is cyclobutyl carbinol.

According to a fourteenth embodiment, the invention relates to a method according to embodiment 12, wherein the brominated compound recovered comprises, by weight relative to the total weight, less than 0.2% of impurities chosen among 4-bromobut-1-ene and bromocyclobutane.

According to a fifteenth embodiment, the invention also provides an adduct of general formula (II):

$$TPP_xTPOP_{(1-x)}Br_{2(p)} \tag{II}$$

wherein
TPP designates triphenylphosphine;
TPOP designates triphenyl phosphite; and
x is a real number comprised between 0.05 and 0.9,
p is equal to 1 or 2.

Finally a sixteenth embodiment of the invention relates to the use of the adduct according to embodiment 15 for bromination of primary alcohol, in particular cyclopropylmethanol or cyclobutylmethanol.

In the present description, unless otherwise indicated, all the percentages (%) are % by mass.

In the present description, unless otherwise indicated, the pressure is atmospheric pressure.

In the present description, "ambient temperature" means a temperature comprised between 15° C. and 40° C., preferably between 20° C. and 30° C., especially approximately 25° C.

Furthermore, any value interval designated by the expression "between a and b" represents the range of values from a to b (i.e., including the strict limits a and b).

In the present invention "adduct" of formula (I) designates the addition product resulting from the addition of x parts by mole of triphenylphosphine and (1-x) parts by mole of triphenyl phosphite. In particular, it designates the addition product resulting from the addition of x parts by mole of triphenylphosphine into (1-x) parts by mole of triphenyl phosphite at a temperature Tx comprised between 20° C. and 50° C. More particularly, the adduct according to the present invention is a mixture consisting of x parts by mole of triphenylphosphine and (1-x) parts by mole of triphenyl phosphite. This mixture representing the adduct is usable and used as liquid reagent, or agent, in a method for primary alcohol bromination, in particular cyclopropylmethanol or cyclobutylmethanol.

Another subject of the invention is adducts obtained by reacting dibromine and adducts of formula (I), $TPOP_{(1-x)}TPP_x$, usable as bromination agents, in particular for primary alcohols.

The quantities expressed in the present description in equivalents correspond to molar equivalents relative to the primary alcohol used, in particular cyclopropylmethanol or cyclobutylmethanol.

DETAILED DESCRIPTION OF THE INVENTION

The invention has for a subject an adduct of general formula (I)

$$TPP_xTPOP_{(1-x)} \quad (I)$$

wherein
TPP designates triphenylphosphine;
TPOP designates triphenyl phosphite; and
x is a real number comprised between 0.05 and 0.9.
TPP corresponds to formula (III) described previously and TPOP corresponds to formula (II) described previously.

Advantageously, x is comprised between 0.05 and 0.5, especially between 0.2 and 0.5.

Advantageously, x is strictly less than 0.5.

The adduct of general formula (I) is advantageously liquid at a temperature comprised between −20° C. and 50° C., making it suitable for use in industrial synthesis.

The adduct of general formula $TPP_xTPOP_{(1-x)}$ is obtained by mixing x parts by mole of triphenylphosphine and (1−x) parts by mole of triphenyl phosphite. In particular, the adduct of general formula $TPP_xTPOP_{(1-x)}$ is obtained by mixing x parts by mole of triphenylphosphine in (1−x) parts by mole of triphenyl phosphite. For reasons of viscosity, this mixture advantageously takes place at a temperature Tx comprised between 20° C. and 50° C., more advantageously between 25° C. and 50° C.

Preferably, between 0.2 and 0.5 parts by mole of triphenylphosphine and between 0.8 and 0.5 parts by mole of triphenyl phosphite will be used.

Otherwise formulated, the invention has for a subject an adduct of general formula (I)

$$TPP_xTPOP_{(1-x)} \quad (I)$$

wherein
TPP designates triphenylphosphine;
TPOP designates triphenyl phosphite; and
x is a real number comprised between 0.05 and 0.9,
obtained by mixing x parts by mole of triphenylphosphine and (1−x) parts by mole of triphenyl phosphite.

Particularly, and given the fact that triphenylphosphine is solid and triphenyl phosphite is liquid at ambient temperature (approx. 20 to 25° C.) and atmospheric pressure (approx. 760 mm Hg), the adduct of general formula (I) according to the invention is obtained by solubilizing x parts of triphenylphosphine in (1−x) parts by mole of triphenyl phosphite.

Since triphenylphosphine is solid (and poorly soluble in the reaction medium), a loss of productivity is possible. This solubility-miscibility difference is even greater due to the fact of the low temperatures used in order to obtain good selectivity. Triphenyl phosphite therefore plays the role of solvent (liquid at ambient temperature) and reagent in bromination. This is why we can think that adduct (I) according to the invention represents a solvation adduct, because in fact, triphenylphosphine is solvated by triphenyl phosphate during this solubilization.

The addition of triphenylphosphine into triphenyl phosphite therefore leads to the formation of an adduct of general formula triphenylphosphine$_{(x)}$-triphenyl phosphite$_{(1-x)}$, also denoted $TPP_{(x)}TPOP_{(1-x)}$.

The molar mass $M_x$ of the adduct is calculated according to the formula: $M_x = x*262 + (1-x)*310$ g/mol.

The applicant will not formulate a hypothesis as to the structure of this adduct (I), but assumes that such an adduct, once brought into contact with the dibromine, will give a structure of the type:

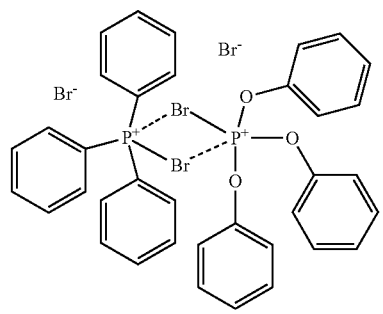

which can have reactivities different from those obtained with dibromine and TPP (x=1) or with dibromine and TPOP (x=0). The discovery of the differences of reactivity clearly shows that it is not obvious for the skilled person to predict the behavior of the adduct according to the invention relative to the pure products, TPP or TPOP.

Another subject of the present invention is to provide an adduct of general formula (II):

$$TPP_xTPOP_{(1-x)} \quad (I)$$

wherein
TPP designates triphenylphosphine;
TPOP designates triphenyl phosphite; and
x is a real number comprised between 0.05 and 0.9,
p is equal to 1 or 2.

Such an adduct according to formula (II) can be obtained by mixing 1 molar equivalent of the adduct of formula (I), optionally diluted in 1 to 3 volumes of a polar solvent, with p molar equivalents of $Br_2$.

The polar solvent is advantageously chosen from among dimethylformamide, dimethyl sulfoxide, sulfolane, dichloromethane, tetrahydrofuran, dimethyl glycol ether, dichloroethane, acetonitrile, and mixtures thereof.

The present invention further concerns the use of an adduct of general formula (II) for bromination of the primary alcohol, in particular cyclopropylmethanol or cyclobutylmethanol.

Surprisingly, it was discovered that this adduct (I) is an excellent reducer, particularly suited to the bromination of primary alcohol, in particular primary alcohol comprising a hydrocarbon ring with 3 or 4 carbon atoms, such as cyclopropyl carbinol or cyclobutyl carbinol. This adduct (I) makes it possible to have higher yields and improved productivity relative to TPP alone or TPOP alone.

The invention also has for a subject a method for preparing adduct (I), or adduct (II), according to the invention, wherein x parts by mole of triphenylphosphine and (1−x) parts by mole of triphenyl phosphite are mixed, at a temperature Tx comprised between 20° C. and 50° C. In particular, x parts by mole of triphenylphosphine are added into (1−x) parts by mole of triphenyl phosphite, at a temperature Tx comprised between 20° C. and 50° C.

The temperature Tx of the mixture for the formation of this adduct is chosen so that mixing is done without viscosity problems. Thus, to have more than 0.5 parts by mole of triphenylphosphine, leading to a compound of formula (I) wherein x is strictly less than 0.5, a temperature of 25° C. or less than 25° C. can be used.

An adduct according to formula (II) can be obtained by mixing 1 molar equivalent of the adduct of formula (I) thus obtained, optionally diluted in 1 to 3 volumes of a polar solvent, with p molar equivalents of $Br_2$. The invention also relates to the use of such an adduct (II) or an adduct (II) thus obtained, as a liquid agent or liquid reagent, for the bromination of primary alcohol.

The polar solvent is advantageously chosen from among dimethylformamide, dimethyl sulfoxide, sulfolane, dichloromethane, tetrahydrofuran, dimethyl glycol ether, dichloroethane, acetonitrile, and mixtures thereof.

Advantageously, in formula (I) or (II), x will be comprised between 0.05 and 0.8, more particularly between 0.05 and 0.5, especially 0.1 to 0.5, or more especially between 0.2 and 0.5. It has been noted that given the solubility of triphenylphosphine at ambient temperature, x will advantageously be comprised between 0.05 and 0.4, especially 0.05 and 0.4, more especially 0.1 and 0.4. In fact, beyond 0.4 and at ambient temperature, solubility difficulties may be encountered. In a particularly preferred manner, x is comprised between 0.05 and 0.3, especially between 0.1 and 0.3, more especially between 0.2 and 0.3.

Such a range for the value of x minimizes residual primary alcohol, maximizes the quantity of brominated final product and limits impurities such as 4-bromo-1-butene and bromocyclobutane to very low (even nondetectable) values.

The invention also has for a subject the use of an adduct (I) or (II) according to the invention or the adduct obtained by the method according to the invention as a liquid agent, or liquid reagent, for the bromination of primary alcohol.

The primary alcohol advantageously comprises a hydrocarbon ring with 3 or 4 carbon atoms, in particular, the primary alcohol is cyclopropylmethanol or cyclobutylmethanol.

Thus the invention also has for a subject a preparation method for a brominated compound (A) by bromination of primary alcohol comprising the following steps:
1 Mixing (a) 1 molar equivalent of adduct (I) according to the invention or the adduct obtained by the method according to the invention and (b) 1 to 3 volumes of polar solvent; then
2 Adding the dibromine:
  2.1 cool with stirring the solution obtained in step 1) to a temperature comprised between 0° C. and 12° C., then
  2.2 to the cooled solution obtained after step 2.1), add between 1.05 and 1.25 molar equivalents of dibromine while keeping the reaction medium temperature below 12° C.; then
3 Adding the primary alcohol:
  3.1 following step 2.2), lower the reaction medium temperature to a value comprised between 0° C. and −15° C.;
  3.2 to the cooled reaction medium obtained following step 3.1), add between 0.95 and 1 molar equivalent of primary alcohol, then
4 Recovering brominated compound (A).

In a first step, one equivalent of adduct (I) is mixed into a polar solvent. The dilution volume is comprised between 1 and 3 volumes relative to adduct (I). The addition of solvent makes it possible to dilute the reaction medium in view of the subsequent addition of alcohol. In the case of only obtaining adduct (II), said solvent is optional as explained above.

The polar solvent is advantageously chosen from among dimethylformamide, dimethyl sulfoxide, sulfolane, dichloromethane, tetrahydrofuran, dimethyl glycol ether, dichloroethane, acetonitrile, and mixtures thereof.

Step 1) is advantageously performed at ambient temperature.

In a second step of this method, dibromine is added to the solution comprising adduct (I), advantageously diluted in a polar solvent, permitting the formation of adduct (II).

This second step comprises first a step 2.1) of cooling, before any addition of dibromine, then the dibromine is added (step 2.2)).

During this step 2.2), the temperature of the reaction medium is advantageously maintained between 0° C. and 12° C. Thus the dibromine is advantageously added slowly, i.e., at a speed such that the temperature of the reaction medium does not exceed 12° C.

Advantageously, following step 2.2), i.e., after dibromine addition is completed, and before step 3), the reaction medium is stirred until adduct (I) disappears. The reaction is instantaneous and the conversion of adduct (I), of formula TPOP(1−x)TPPx, into adduct (II), of formula TPOP(1−x)TPPx.$Br_2$ is quantitative In a third step, the primary alcohol is added.

This third step comprises first a step 3.1) of cooling, before any addition of primary alcohol, then the primary alcohol is added (step 3.2)).

During step 3.1), the temperature of the reaction medium is lowered to a value comprised between 0° C. and −15° C., advantageously comprised between 0° C. and −5° C.

Then, during step 3.2), a primary alcohol, such as cyclopropylmethanol or cyclobutylmethanol, is added to the reaction medium.

During this step 3.2), the temperature of the reaction medium is advantageously maintained at a target value comprised between 0° C. and −15° C., advantageously comprised between 0° C. and −5° C. Thus the primary alcohol is advantageously added slowly, i.e., at a speed such that the temperature of the reaction medium is maintained at the target value.

Stirring is then advantageously maintained for the reaction medium, advantageously at a temperature corresponding to the target value of step 3.2), until complete consumption of the primary alcohol. Then, the reaction medium is advantageously brought to ambient temperature.

During step 4), brominated compound (A) is recovered, for example by following the steps described in patent FR3016166.

Thus, for example, the reaction medium, brought to ambient temperature, containing compound (A) is subjected to a distillation according to methods known to the skilled person. For example, this distillation can be done by heating under reduced pressure. The distillation temperature can be comprised between 50 and 70° C., more particularly at approximately 65° C. and at a pressure comprised between 1 mbar and 10 mbar, more particularly at approximately 5 mbar.

After distillation, the fractions containing brominated compound (A) can be washed and then dried.

Brominated compound (A) can be washed by any suitable means known to the skilled person, for example using a buffer solution at pH 8, such as a sodium or potassium carbonate solution.

Brominated compound (A) once washed can be dried using a desiccant in a way known to the skilled person. The desiccant can be chosen from among silica gels, calcium chloride, magnesium chloride, zeolites, lithium chloride or lithium bromide, for example. The present method has the advantage of providing a brominated compound (A) with a level of purity greater than 95%, particularly greater than 97%, more particularly greater than 98%. Such a level of purity is particularly advantageous regarding the use of a brominated compound (A) in the final synthesis steps for active pharmaceutical ingredients for which a high purity is required. In particular, for BMCP, the level of impurities chosen from among 4-bromobut-1-ene and bromocyclobutane is less than 0.2%.

The yields obtained via the method according to the present invention, relative to the initial primary alcohol, are greater than 80%, which is singularly advantageous in an industrial context and particularly unexpected.

The interest of this method is to arrive at very low levels of impurities, for BMCP less than 0.2% of impurities chosen from among 4-bromobut-1-ene and bromocyclobutane, as in patent U.S. 61/913,001 but with yields greater than 80% relative to the initial primary alcohol. Furthermore, one will benefit from the fact that $TPP_xTPOP_{(1-x)}$ makes it possible to react more primary alcohol in the same reaction volume as a method according to FR3016166 or FR3010997. For example for x=0.4 a gain of 8% of product transformed in the same reactor is obtained and for x=0.2 a gain of 4% of product transformed in the same reactor is obtained. Therefore, a very productive and very selective method is obtained, which was not at all obvious for the skilled person.

The method according to the present invention and the advantages thereof will be better understood by means of the following illustrative examples.

EXAMPLES

The raw materials are the raw materials found at Sigma Aldrich.

The analytical method consists of analysis by gas chromatography (GC) on a HP 5890 Series II device. The chromatography column is a Optima delta 6, 30 m, 0.25 mm, 0.25 μm column.

The oven has the following temperature profile: Initial temperature: 40° C., Initial time 5 min. Gradient 5°/min; Final temperature: 125° C. Duration 15 min.

The injector temperature is 250° C., the detector temperature is 280° C., the volume injected is 1 μL and the pressure is 6 psi. The sample concentration is 75 g/L in tetrahydrofuran (THF).

The reactions are performed in a 20-L double-walled glass reactor and the distillations are done by means of a glass column with 10 theoretical plateaus.

Example 1: Preparation of Adduct (I) $TPP_xTPOP_{(1-x)}$

Quantities x of triphenylphosphine in (1−x) parts by mole of triphenyl phosphite are loaded into a clean, dry reactor under nitrogen, equipped with a stirrer, at temperatures Tx according to the following table.

TABLE 1

| x | 0.1 | 0.2 | 0.3 | 0.4 | 0.5 | 0.6 | 0.7 | 0.8 |
|---|---|---|---|---|---|---|---|---|
| Tx (° C.) | 25 | 25 | 25 | 25 | 45 | 50 | 55 | 55 |

After homogenization, the mixture is brought to room temperature if necessary. It can be stored in the liquid state for later use.

The fact that TPP is solubilized by TPOP is characteristic of the weak interactions between the molecules of each species, which characterizes an adduct.

Example 2: Use of the $TPP_{0.2}TPOP_{(0.8)}$ Adduct for the Production of BMCP 4.63 kg of DMF (1.1 eqV), then 4.53 kg of adduct (15.1 mol) are successively introduced into a 20-L reactor. Then 2.74 kg (17 mol) of dibromine are introduced while maintaining the temperature below 12° C. The stirring speed is set according to the fluidity of the reaction medium. At the end of the run, a very thick medium is obtained with a yellow solid in suspension.

The double wall is then set at −12° C., and 1.054 kg (14.6 mol) of cyclopropylmethanol are introduced so as not to exceed a temperature of −5° C. At the end of the addition, the temperature is allowed to slowly return to ambient temperature. Then, the double wall is set to 64° C. for the distillation. This distillation is done at a pressure of 13 mbar by collecting the first fraction at 24 to 30° C. at the top of the column, then the second fraction at 30 to 40° C. (partial reflux). Two fractions F1 (1.77 kg) and F2 (340 g) are collected. After washing in carbonated water then drying by $CaCl_2$, the two fractions lead to BMCP (masse 1.664 kg, 12.05 mol) of relative GC purity of 98.9%, with a yield of 82%. The amount of bromobutene measured is 0.09%, the amount of bromocyclobutane is 0.10%.

Comparative Example 1: Method According to Patent FR3016166

4.63 kg of DMF (5.1 eqV), then 4.53 kg of triphenyl phosphite are loaded successively into a clean, dry reactor, under nitrogen and equipped with a stirrer. Then 2.34 kg of dibromine are introduced while maintaining the temperature below 12° C. The stirring speed is set according to the fluidity of the reaction medium. At the end of the run, a very thick medium is obtained with a yellow solid in suspension.

The double wall is then set at −12° C., and 0.96 kg of cyclopropylmethanol are introduced so as not to exceed a temperature of −5° C. At the end of the addition, the temperature is allowed to slowly return to ambient temperature. Then, the double wall is set to 64° C. for the distillation. This distillation is done at a pressure of 13 mbar by collecting the first fraction at 24 to 30° C. at the top of the column, then the second fraction at 30 to 40° C. (partial reflux). Two fractions F1 (1.38 kg) and F2 (293 g) are collected. After washing in carbonated water then drying by $CaCl_2$, the two fractions lead to a final product 2a (mass 1.316 kg) of relative GC purity of 98.7%, with a yield of 73%.

The comparison between Example 2 and Comparative Example 1 shows: a higher yield of 9% and a higher committed raw material rate of 4%, which contributes to increasing the production per liter of usable reactor from 65.8 g/L to 83.2 g/L.

Example 3: Characterization of the Specific Reactivity of Adducts (I) with Dibromine So as to demonstrate the difference in behavior of pure TPP or TPOP relative to adducts (I) according to the invention, we conducted the following experiment.

Test A: We added 0.5 mL of anhydrous deuterated DMF then 40 mg of $TPP_{0.5}TPOP_{0.5}$ into an NMR tube. The tube was cooled to 0° C. and we then added 11 mg of dibromine. We then carried out a phosphorus NMR and the observed chemical shift is difficult to define because the signal is broad (between 15 and 19 ppm)

Test B: We added 1 mL of anhydrous deuterated DMF then 40 mg of TPP into an NMR tube. The tube was cooled to 0° C. and we then added 11 mg of dibromine. We then carried out a phosphorus NMR. The chemical shift observed is −16 ppm.

Test C: We added 0.5 mL of anhydrous deuterated DMF then 40 mg of TPOP into an NMR tube. The tube was cooled to 0° C. and we then added 11 mg of dibromine. We then carried out a phosphorus NMR. The chemical shift observed is −18 ppm.

These three experiments show that the $TPP_{0.5}TPOP_{0.5}$ adduct leads, by reaction with dibromine, to a different adduct from those obtained by pure TPOP or pure TPP. This experiment shows that mixed $TPPBr_2$-$TPOPBr_2$ compounds interact and form mixed species in solution, which could explain the different reactivity of adducts (I) relative to the pure TPP or TPOP species.

Example 4

By repeating the experimental conditions of Example 1, the yields and impurities are assessed according to different values of X.

For X greater than 0.4, the mixture of triphenylphosphine in triphenyl phosphite exhibits solubility difficulties at ambient temperature. Since we wish to remain at ambient temperature, the value of X=0.4 is the limit for the present tests. X=0 represents the method according to the prior art. Laboratory tests lead to the following results:

|  | Initial alcohol | Final product | 4-bromobut-1-ene | Bromocyclobutane |
| --- | --- | --- | --- | --- |
| X = 0 | 0.51% | 86% | ND | 0.25% |
| X = 0.1 | 2.16% | 88% | 0.09% | 0.24% |
| X = 0.2 | 2.09% | 84% | ND | ND |
| X = 0.3 | 3.59% | 88% | ND | ND |

ND: not detected

Since the bromocyclopropane content produced is comparable but the conversion is a little lower with the addition of triphenylphosphine, this implies that at equal conversion, the purity is greater. Moreover, the 4-bromobut-1-ene and bromocyclobutane impurities are absent at a higher content of triphenylphosphine.

The invention claimed is:

1. Adduct of general formula (I)

$$TPP_xTPOP_{(1-x)} \quad (I)$$

wherein
TPP designates triphenylphosphine;
TPOP designates triphenyl phosphite; and
x is a real number comprised between 0.05 and 0.9.

2. Adduct according to claim 1, for which x is comprised between 0.05 and 0.5.

3. Preparation method for the adduct according to claim 1, wherein x parts by mole of triphenylphosphine and (1-x) parts by mole of triphenyl phosphite are mixed at a temperature Tx comprised between 20° C. and 50° C.

4. Preparation method according to claim 3, wherein Tx is 25° C. and x<0.5.

5. Preparation method for a compound brominated by bromination of a primary alcohol comprising the following steps:
  1) mixing (a) 1 molar equivalent of adduct (I) according to claim 1 and (b) 1 to 3 volumes of polar solvent; then
  2) adding dibromine:
    2.1) cool with stirring the solution obtained in step 1) to a temperature comprised between 0° C. and 12° C., then
    2.2) to the cooled solution obtained after step 2.1), add between 1.05 and 1.25 molar equivalents of dibromine while keeping the reaction medium temperature below 12° C.; then
  3) adding the primary alcohol:
    3.1) following step 2.2), lower the reaction medium temperature to a value comprised between 0° C. and −15° C.;
    3.2) to the cooled reaction medium obtained following step 3.1), add between 0.95 and 1 molar equivalent of primary alcohol, then
  4) Recovering brominated compound (A).

6. Method according to claim 5, wherein the polar solvent is chosen from among dimethylformamide, dimethyl sulfoxide, sulfolane, dichloromethane, tetrahydrofuran, dimethyl glycol ether, dichloroethane, acetonitrile, and mixtures thereof.

7. Method according to claim 5, wherein during step 2.2) the reaction medium is maintained at a temperature comprised between 0° C. and 12° C.

8. Method according to claim 5, wherein during step 3.2) the reaction medium is maintained at a temperature comprised between 0° C. and −15° C.

9. Method according to claim 5, wherein the primary alcohol comprises a hydrocarbon ring with 3 or 4 carbon atoms.

10. Method according to claim 5 wherein the primary alcohol is cyclopropyl carbinol.

11. Method according to claim 5 wherein the primary alcohol is cyclobutyl carbinol.

12. Method according to claim 10, wherein the brominated compound recovered comprises, by weight relative to the total weight, less than 0.2% of impurities chosen among 4-bromobut-1-ene and bromocyclobutane.

13. Adduct of general formula (II)

$$TPP_xTPOP_{(1-x)}Br_{2(p)} \quad (II)$$

wherein
TPP designates triphenylphosphine;
TPOP designates triphenyl phosphite; and
x is a real number comprised between 0.05 and 0.9;
p is equal to 1 or 2.

14. Use of the adduct according to claim 13 for bromination of primary alcohol, in particular cyclopropylmethanol or cyclobutylmethanol.

* * * * *